United States Patent
Inoue et al.

(10) Patent No.: US 10,952,893 B2
(45) Date of Patent: Mar. 23, 2021

(54) MULTILAYER FILM FOR DISPOSABLE BODY WARMER OUTER BAG, AND DISPOSABLE BODY WARMER

(71) Applicants: KOBAYASHI PHARMACEUTICAL CO., LTD., Osaka (JP); KANAOKA CO., LTD., Tokyo (JP)

(72) Inventors: Hiroyuki Inoue, Tokyo (JP); Takayuki Miyazaki, Tokyo (JP); Tsuyoshi Igaue, Osaka (JP); Yorikazu Kotani, Osaka (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 383 days.

(21) Appl. No.: 15/329,930

(22) PCT Filed: Jul. 30, 2015

(86) PCT No.: PCT/JP2015/071602
§ 371 (c)(1),
(2) Date: Jan. 27, 2017

(87) PCT Pub. No.: WO2016/017733
PCT Pub. Date: Feb. 4, 2016

(65) Prior Publication Data
US 2017/0258632 A1    Sep. 14, 2017

(30) Foreign Application Priority Data
Jul. 31, 2014 (JP) .............................. JP2014-157228

(51) Int. Cl.
*A61F 7/03* (2006.01)
*B65D 65/40* (2006.01)
(Continued)

(52) U.S. Cl.
CPC ............... *A61F 7/03* (2013.01); *B32B 3/266* (2013.01); *B32B 5/022* (2013.01); *B32B 5/024* (2013.01);
(Continued)

(58) Field of Classification Search
CPC combination set(s) only.
See application file for complete search history.

(56) References Cited

U.S. PATENT DOCUMENTS 9,024,360 B1 * 5/2015 Huffer .................... A47J 36/28
257/211
2005/0244629 A1 * 11/2005 Usui ........................ A61F 7/034
428/323

(Continued)

FOREIGN PATENT DOCUMENTS

EP    0 787 821 A2    8/1997
JP    4-309941 A     11/1992
(Continued)

OTHER PUBLICATIONS

Database WPI, Week 200247, Thomson Scientific, London, GB; AN 2002-439607, XP002775304 (JP 2002-086614 A, Mar. 26, 2002, Abstract).

(Continued)

*Primary Examiner* — Joseph A Stoklosa
*Assistant Examiner* — Adam J Avigan
(74) *Attorney, Agent, or Firm* — Birch, Stewart, Kolasch & Birch, LLP

(57) ABSTRACT

To provide a multilayer film for a disposable body warmer outer bag, and a disposable body warmer that are excellent in gas barrier property which inhibits permeation of oxygen gas, water vapor and the like, and that can allow swelling due to hydrogen gas generated during a storage period to be prevented.

(Continued)

In a disposable body warmer outer bag formed from a multilayer film including a sealant layer 10 and a barrier layer 20, the sealant layer 10 and the barrier layer 20 serve as an inner surface and an outer surface of the outer bag, respectively. The sealant layer 10 includes a vapor-deposited layer 12 made by vapor-depositing a metal or metal oxide on at least one surface (upper portion in FIG. 1) of a thermal fusible resin substrate 11. The barrier layer 20 includes a polyvinylidene chloride layer 22 made by coating at least one surface (lower portion in FIG. 1) of a heat-resistant resin substrate 21 with polyvinylidene chloride.

8 Claims, 2 Drawing Sheets

(51) Int. Cl.

| | |
|---|---|
| B32B 27/30 | (2006.01) |
| B32B 3/26 | (2006.01) |
| B32B 9/00 | (2006.01) |
| B32B 27/08 | (2006.01) |
| B32B 27/36 | (2006.01) |
| B32B 23/08 | (2006.01) |
| B32B 27/40 | (2006.01) |
| B32B 27/32 | (2006.01) |
| B65D 81/24 | (2006.01) |
| B32B 27/12 | (2006.01) |
| B32B 5/02 | (2006.01) |
| B32B 27/28 | (2006.01) |
| B32B 27/34 | (2006.01) |
| C08J 7/04 | (2020.01) |
| B32B 7/12 | (2006.01) |
| B32B 37/12 | (2006.01) |
| A61F 7/02 | (2006.01) |

(52) U.S. Cl.
CPC .................. *B32B 7/12* (2013.01); *B32B 9/00* (2013.01); *B32B 23/08* (2013.01); *B32B 27/08* (2013.01); *B32B 27/12* (2013.01); *B32B 27/28* (2013.01); *B32B 27/30* (2013.01); *B32B 27/302* (2013.01); *B32B 27/304* (2013.01); *B32B 27/306* (2013.01); *B32B 27/308* (2013.01); *B32B 27/32* (2013.01); *B32B 27/325* (2013.01); *B32B 27/34* (2013.01); *B32B 27/36* (2013.01); *B32B 27/365* (2013.01); *B32B 27/40* (2013.01); *B32B 37/12* (2013.01); *B65D 65/40* (2013.01); *B65D 81/24* (2013.01); *C08J 7/0423* (2020.01); *A61F 2007/0222* (2013.01); *A61F 2007/0258* (2013.01); *B32B 2250/02* (2013.01); *B32B 2250/03* (2013.01); *B32B 2250/24* (2013.01); *B32B 2250/246* (2013.01); *B32B 2255/10* (2013.01); *B32B 2255/20* (2013.01); *B32B 2255/205* (2013.01); *B32B 2255/26* (2013.01); *B32B 2307/306* (2013.01); *B32B 2307/31* (2013.01); *B32B 2307/518* (2013.01); *B32B 2307/724* (2013.01); *B32B 2307/7244* (2013.01); *B32B 2307/7246* (2013.01); *B32B 2307/732* (2013.01); *B32B 2439/06* (2013.01); *B32B 2439/46* (2013.01); *B32B 2571/00* (2013.01); *C08J 2427/08* (2013.01)

(56) References Cited

U.S. PATENT DOCUMENTS

| | | | |
|---|---|---|---|
| 2011/0052867 A1* | 3/2011 | Yamamura | B32B 27/08 428/141 |
| 2013/0004760 A1 | 1/2013 | Pellingra | |

FOREIGN PATENT DOCUMENTS

| | | | |
|---|---|---|---|
| JP | 2002-86607 A | | 3/2002 |
| JP | 2002-86614 A | | 3/2002 |
| JP | 2002-120860 A | | 4/2002 |
| JP | 2006-347582 A | | 12/2006 |
| JP | 2007-136736 A | | 6/2007 |
| JP | 2008-72529 A | | 4/2008 |
| JP | 2008-143103 A | | 6/2008 |
| JP | 2008143103 A | * | 6/2008 |
| JP | 2012-65876 A | | 4/2012 |

OTHER PUBLICATIONS

Extended European Search Report dated Nov. 15, 2017, in European Patent Application No. 15826638.7.
International Search Report for PCT/JP2015/071602 dated Sep. 1, 2015.
Written Opinion of the International Searching Authority for PCT/JP2015/071602 (PCT/ISA/237) dated Sep. 1, 2015.

* cited by examiner

MULTILAYER FILM FOR DISPOSABLE BODY WARMER OUTER BAG, AND DISPOSABLE BODY WARMER

TECHNICAL FIELD

The present invention relates to a multilayer film for a disposable body warmer outer bag, and a disposable body warmer.

BACKGROUND ART

A disposable body warmer is a body warmer utilizing heat generation due to the oxidation action of iron powder. In general, the disposable body warmer includes an outer bag made of air-impermeable film and an air-permeable inner bag of a non-woven fabric, paper or the like. The inner bag is accommodated and packaged airtightly in the outer bag. The inner bag contains an exothermic composition containing iron powder as an exothermic element, a salt as an oxidation catalyst, activated carbon for intake of oxygen, water for oxidizing iron, a water-retaining agent for retaining water, and the like. The outer bag cuts off contact with air in an unused state.

A disposable body warmer outer bag is required to be excellent in gas barrier property that inhibits permeation of air, especially, oxygen gas, water vapor, and the like. If the disposable body warmer outer bag is poor in gas barrier property against oxygen gas and water vapor, any gas and water vapor in the disposable body warmer outer bag escape outside during storage for a long period to thereby produce a depressurized (vacuum) state, and therefore the outer bag is depressed and thus is not preferable in terms of appearance. In addition, when such a disposable body warmer outer bag in a depressurized (vacuum) state is stored for a long period and thereafter used for a disposable body warmer, the duration of heat generation is often short. As the air-impermeable film forming the disposable body warmer outer bag, a multilayer film is generally used where a gas barrier layer is provided on a sealant layer and a heat-resistant resin layer is provided on an outermost layer. Two of such air-impermeable multilayer films are superposed and the peripheries of the sealant layers located inward are mutually heat-sealed to form a bag, thereby producing the disposable body warmer outer bag.

As the air-impermeable film forming such a disposable body warmer outer bag, for example, a multilayer film is proposed where an inorganic oxide vapor-deposited film is provided on one surface of a substrate film being a biaxially oriented polyester-based resin film, a biaxially oriented polyamide-based resin film or a biaxially oriented polyolefin-based resin film, and a primer agent layer, a printing pattern layer, and a heat-sealing resin layer of polyethylene or the like are sequentially provided on the vapor-deposited film (Patent Literatures 1 to 2). In this multilayer film, the substrate film on which an inorganic oxide is vapor-deposited serves as a gas barrier layer, and the heat-sealing resin layer serves as a sealant layer.

Meanwhile, it is known that, when a disposable body warmer is stored in an unused state for a long period, a trace amount of hydrogen gas is generated. A disposable body warmer outer bag is swollen by hydrogen gas, and is not preferable in terms of appearance. Therefore, the disposable body warmer outer bag is required to have a hydrogen permeation property so that the outer bag is not swollen during storage for a long period. The disposable body warmer outer bag, however, is also required to be excellent in gas barrier property that inhibits permeation of oxygen gas, water vapor and the like, as described above. Therefore, if the gas barrier property of the air-impermeable film forming the disposable body warmer outer bag is enhanced, a hydrogen gas permeation property is deteriorated to result in swelling during storage for a long period. There is then proposed as one that satisfies both conflicting conditions of a gas barrier property against oxygen gas and water vapor and a hydrogen gas permeation property, an outer bag for a disposable body warmer, made by adopting a biaxially oriented polyethylene terephthalate film as an outermost layer, and dry laminating a first metal vapor-deposited film layer where aluminum is vapor-deposited on biaxially oriented polypropylene (OPP), inward against the outermost layer, and a second metal vapor-deposited film layer where aluminum is vapor-deposited on unoriented polypropylene (CPP), inward against and apart from the outermost layer (Patent Literature 3). In such a multilayer film, the first metal vapor-deposited film layer serves as a barrier layer and the second metal vapor-deposited film layer serves as a sealant layer.

The outer bag for a disposable body warmer described in Patent Literature 3, however, has the following problem: aluminum is difficult to vapor-deposit on the OPP film located closer to the outer layer and furthermore the CPP film being an inner layer is more easily oriented because of being poorer in tensile strength and tearing strength than the OPP film oriented, thereby causing the aluminum vapor-deposited film to be cracked during a production process, to make it impossible to ensure a high gas barrier property. There is then proposed an outer bag for a disposable body warmer, made by adopting biaxially oriented polypropylene as a substrate film, and laminating a barrier film having an aluminum oxide vapor-deposited film on the outer surface of polyethylene terephthalate, and a sealant resin layer of polyethylene or the like, inward against the substrate film (Patent Literature 4). The outer bag for a disposable body warmer described in Patent Literature 4, however, has been found to be incapable of penetration of hydrogen gas generated, and thus be swollen. If marginally swollen, the outer bag is broken, and an exothermic composition accommodated in an inner bag is oxidized to generate heat, thereby causing the function as a disposable body warmer to be impaired.

As described above, various multilayer films for disposable body warmer outer bag are proposed, but a multilayer film for a disposable body warmer outer bag, and a disposable body warmer are required which can ensure an optimum gas permeation property and gas barrier property as a product over a long period.

CITATION LIST

Patent Literatures

Patent Literature 1: Japanese Patent Laid-Open No. 2002-086607
Patent Literature 2: Japanese Patent Laid-Open No. 2002-120860
Patent Literature 3: Japanese Patent Laid-Open No. 2006-347582
Patent Literature 4: Japanese Patent Laid-Open No. 2012-065876

SUMMARY OF INVENTION

Technical Problem

An object of the present invention is then to provide a multilayer film for a disposable body warmer outer bag, and a disposable body warmer that are excellent in gas barrier property which inhibits permeation of oxygen gas, water vapor and the like, and that can allow swelling due to hydrogen gas generated during storage to be prevented.

Solution to Problem

The present inventors have made intensive studies in order to solve the above problem, and as a result, have found that a multilayer film including a vapor-deposited layer made by vapor-depositing a metal or metal oxide on a substrate, and a polyvinylidene chloride layer made by coating a substrate with polyvinylidene chloride can realize optimum oxygen gas and water vapor permeation properties as a disposable body warmer outer bag, thereby leading to completion of the present invention. In particular, a multilayer film where a sealant layer made by vapor-depositing a metal or metal oxide on a thermal fusible resin and a barrier layer made by coating a heat-resistant resin with polyvinylidene chloride are laminated can realize an optimum gas permeation property and water vapor permeation property which prevent excessive permeation of oxygen gas and water vapor and which allow hydrogen gas to permeate. Specific aspects of the present invention are as follows.

[1] A multilayer film for a disposable body warmer outer bag, comprising a vapor-deposited layer made by vapor-depositing a metal or metal oxide on a substrate, and a polyvinylidene chloride layer made by coating a substrate with polyvinylidene chloride.

[2] The multilayer film for a disposable body warmer outer bag according to [1], wherein the vapor-deposited layer is a sealant layer made by vapor-depositing a metal or metal oxide on at least one surface of a thermal fusible resin substrate, and the polyvinylidene chloride layer is a barrier layer made by coating at least one surface of a heat-resistant resin substrate with polyvinylidene chloride.

[3] The multilayer film for a disposable body warmer outer bag according to [1] or [2], wherein the vapor-deposited layer is made by vapor-depositing a metal or metal oxide on the substrate or the thermal fusible resin substrate selected from unoriented polypropylene, biaxially oriented polypropylene, unoriented polyethylene, low density polyethylene, medium density polyethylene, high density polyethylene and straight-chain (linear) low density polyethylene.

[4] The multilayer film for a disposable body warmer outer bag according to any one of [1] to [3], wherein the vapor-deposited layer is made by vapor-depositing aluminum on the substrate or the thermal fusible resin substrate selected from unoriented polypropylene, biaxially oriented polypropylene, unoriented polyethylene, low density polyethylene, medium density polyethylene, high density polyethylene and straight-chain (linear) low density polyethylene, and the polyvinylidene chloride layer is made by coating the substrate or the heat-resistant resin substrate selected from biaxially oriented polypropylene, biaxially oriented polyethylene terephthalate and biaxially oriented polyamide resins with a polyvinylidene chloride resin.

[5] The multilayer film for a disposable body warmer outer bag according to any one of [1] to [4], further comprising an adhesive layer between the vapor-deposited layer and the polyvinylidene chloride layer.

[6] The multilayer film for a disposable body warmer outer bag according to any one of [1] to [5], comprising an additional resin layer.

[7] The multilayer film for a disposable body warmer outer bag according to any one of [1] to [6], wherein an oxygen permeability measured at 20° C. and 90% RH is 1.5 to 5.0 cc/($m^2$·day·atm), and a water vapor permeability measured at 40° C. and 90% RH is 0.05 to 1.5 g/($m^2$·day).

[8] A disposable body warmer made by packaging airtightly an inner bag accommodating an exothermic composition, in an outer bag formed by thermal fusion of the multilayer film for a disposable body warmer outer bag according to any one of [1] to [7].

Advantageous Effects of Invention

The multilayer film for a disposable body warmer outer bag of the present invention has an optimum gas barrier property for a disposable body warmer outer bag that inhibits permeation of oxygen gas and water vapor and also permits permeation of hydrogen gas.

The disposable body warmer of the present invention can allow swelling due to hydrogen gas generated during storage and degradation of an exothermic composition due to permeation of oxygen gas and water vapor to be prevented, and can allow the function as a disposable body warmer to be prevented from being impaired, even when stored for a long period.

DESCRIPTION OF EMBODIMENTS

Hereinafter, the multilayer film for a disposable body warmer outer bag and the disposable body warmer of the present invention are described with reference to the drawings.

The multilayer film for a disposable body warmer outer bag of the present invention includes a vapor-deposited layer made by vapor-depositing a metal or metal oxide on a substrate, and a polyvinylidene chloride layer made by coating a substrate with polyvinylidene chloride. The substrate on which a metal or metal oxide is vapor-deposited and the substrate coated with polyvinylidene chloride may be the same or different. The vapor-deposited layer and the polyvinylidene chloride layer, when formed into a disposable body warmer outer bag, may be laminated with any of the polyvinylidene chloride layer and the vapor-deposited layer being located inward or outward, but it is preferable that the polyvinylidene chloride layer and the vapor-deposited layer be laminated so as to be located outward and inward, respectively.

Figure 1:
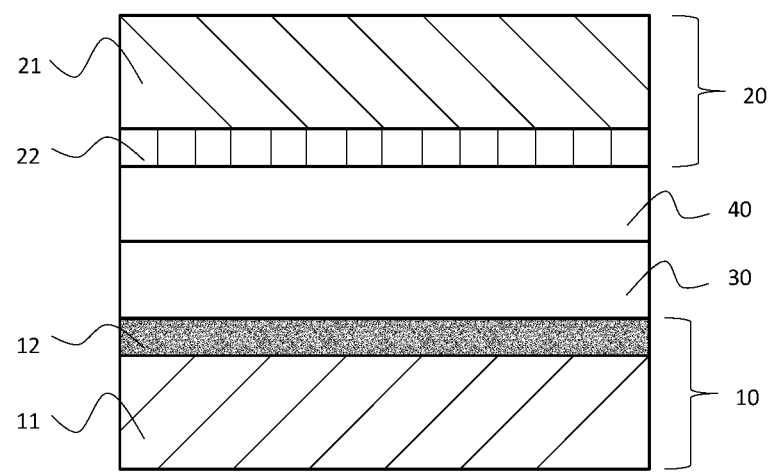
FIG. 1 is an explanatory view illustrating a lamination configuration according to one embodiment of the multilayer film for a disposable body warmer outer bag of the present invention.
Figure 2:
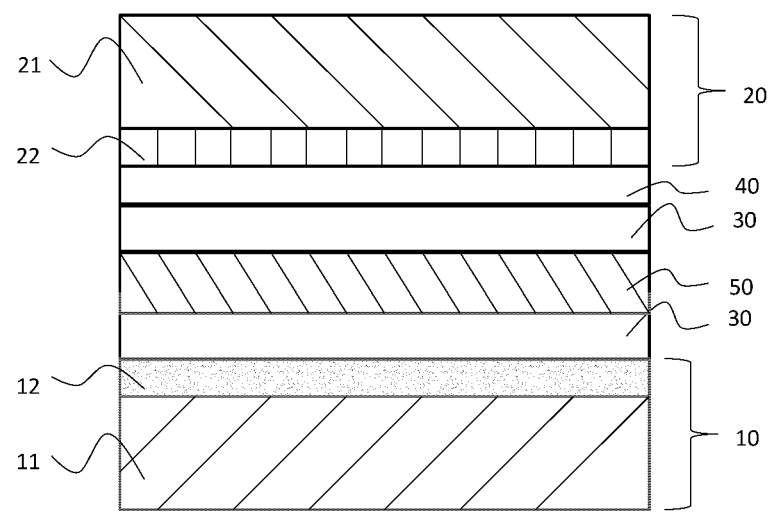
FIG. 2 is an explanatory view illustrating a lamination configuration according to another embodiment of the multilayer film for a disposable body warmer outer bag of the present invention.
Figure 3:
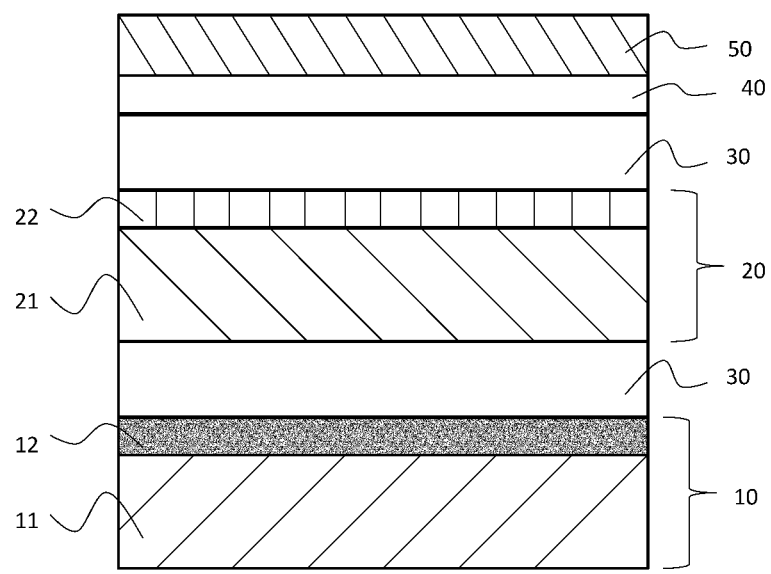
FIG. 3 is an explanatory view illustrating a lamination configuration according to still another embodiment of the multilayer film for a disposable body warmer outer bag of the present invention.

FIGS. 1 to 3 illustrate embodiments of the multilayer film for a disposable body warmer outer bag of the present invention. The multilayer film for a disposable body warmer outer bag includes a sealant layer 10 and a barrier layer 20. In a disposable body warmer outer bag, the sealant layer 10 and the barrier layer 20 serve as an inner surface and an outer surface of the outer bag, respectively.

In FIG. 1, the sealant layer 10 includes a vapor-deposited layer 12 made by vapor-depositing a metal or metal oxide on at least one surface (upper portion in FIG. 1) of a thermal fusible resin substrate 11. The barrier layer 20 includes a polyvinylidene chloride layer 22 made by coating at least one surface (lower portion in FIG. 1) of a heat-resistant resin substrate 21 with polyvinylidene chloride. In the embodiment illustrated in FIG. 1, an adhesive layer 30 and a printing ink layer 40 are laminated on the sealant layer 10. The adhesive layer 30 is used for adhesion of the vapor-deposited layer 12 of the sealant layer 10 to the barrier layer 20 or another layer. The printing ink layer 40 can be, if necessary, provided for printing of item description and the like.

In the embodiment illustrated in FIG. 2, the configuration in FIG. 1 further includes an additional resin layer 50 between the adhesive layer 30 and the printing ink layer 40. The additional resin layer 50 provided therebetween enhances strength of the multilayer film. In addition, the additional resin layer 50 can be provided to thereby increase the entire thickness of the multilayer film, thereby resulting in further decreases in gas permeation property and water vapor permeation property.

In the embodiment illustrated in FIG. 3, an adhesive layer 30 located downward is laminated on the sealant layer 10, the barrier layer 20 is then laminated thereon so that the heat-resistant resin substrate 21 and the polyvinylidene chloride layer 22 are located in this order, and an adhesive layer 30 located upward and the printing ink layer 40 are further interposed in this order and the additional resin layer 50 is laminated so as to serve as an outer lost layer.

A disposable body warmer outer bag configured from the multilayer film for a disposable body warmer outer bag of the present invention illustrated in each of FIGS. 1 to 3 includes the vapor-deposited layer 12 made by vapor-depositing a metal or metal oxide on at least one surface of the thermal fusible resin substrate 11, as the sealant layer 10, and the polyvinylidene chloride layer 22 on at least one surface of the heat-resistant resin substrate 21, as the barrier layer 20, thereby blocking penetration of oxygen from the exterior of the outer bag into the interior of the outer bag at a certain level and permitting permeation of hydrogen from the interior of the outer bag into the exterior of the outer bag. Thus, a metal such as iron powder in an exothermic composition accommodated in a disposable body warmer inner bag is effectively prevented from being oxidized, and also the outer bag is effectively prevented from being swollen due to hydrogen generated during storage. Furthermore, the vinylidene chloride layer 22 and the vapor-deposited layer 12 are provided to thereby enhance a water vapor barrier property that prevents permeation of water vapor. Thus, moisture is prevented from penetrating from the exterior of the outer bag into the interior of the outer bag, and water serving to promote oxidation of a metal such as iron powder included, as a constituent, in the exothermic composition of the disposable body warmer is also prevented from being discharged as water vapor from the interior of the outer bag toward the exterior of the outer bag.

Next, constituents and a production method of the multilayer film for a disposable body warmer outer bag of the present invention are described.

The sealant layer 10 includes the thermal fusible resin substrate 11 and the vapor-deposited layer 12. As the thermal fusible resin, for example, low density polyethylene, medium density polyethylene, high density polyethylene, straight-chain (linear) low density polyethylene, polypropylene, an ethylene-vinyl acetate copolymer, an ionomer resin, an ethylene-ethyl acrylate copolymer, an ethylene-acrylic acid copolymer, an ethylene-methacrylic acid copolymer, an ethylene-propylene copolymer, a methylpentene polymer, and an acid-modified polyolefin-based resin where a polyolefin-based resin such as polyethylene, polystyrene or polypropylene is modified with an unsaturated carboxylic acid such as acrylic acid, methacrylic acid, maleic anhydride or fumaric acid, as well as other resins can be used singly or in combinations of two or more. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. The various resin films can be further uniaxially or biaxially oriented by utilizing, for example, a tentering method or a tubular method. Among them, unoriented polypropylene, biaxially oriented polypropylene, unoriented polyethylene, low density polyethylene, medium density polyethylene, high density polyethylene or straight-chain (linear) low density polyethylene is preferable, and in particular, unoriented polypropylene, biaxially oriented polypropylene or straight-chain (linear) low density polyethylene is more preferable in terms of a thermal fusion property.

In addition, the thickness of the thermal fusible resin substrate 11 is preferably 5 to 300 μm, more preferably 10 to 100 μm, most preferably 15 to 50 μm.

The vapor-deposited layer vapor-deposited on the thermal fusible resin substrate 11 is formed from a metal or metal oxide. Specific examples of the metal vapor-deposited on the thermal fusible resin substrate 11 include aluminum, gold, silver, copper, nickel, chromium, germanium, selenium, titanium, tin and zinc. In addition, specific examples of the metal oxide vapor-deposited on the thermal fusible resin substrate 11 include aluminum oxide and silicon oxide. The metal or metal oxide vapor-deposited on the thermal fusible resin substrate 11 is preferably aluminum, aluminum oxide or silicon oxide in terms of economic efficiency, more preferably aluminum in terms of a gas barrier property, economic efficiency, stability and practicality.

The thickness of the vapor-deposited layer 12 is preferably 50 to 5000 angstroms, more preferably 100 to 1000 angstroms, most preferably 200 to 800 angstroms.

The oxygen permeability (20° C. and 90% RH) of the sealant layer by itself is preferably 10 to 200 cc/(m$^2$·day·atm), more preferably 10 to 150 cc/(m$^2$·day·atm), most preferably 10 to 100 cc/(m$^2$·day·atm). In addition, the water vapor permeability (40° C. and 90% RH) of the sealant layer by itself is preferably 0.05 to 5.0 g/(m$^2$·day), more preferably 0.05 to 3.0 g/(m$^2$·day), most preferably 0.5 to 3.0 g/(m$^2$·day).

For example, a vacuum vapor deposition method, a sputtering method, or an ion plating method can be used as the method for vapor-depositing the metal or metal oxide on the thermal fusible resin substrate 11.

The barrier layer 20 includes the polyvinylidene chloride layer 22 made by coating the heat-resistant resin substrate 21 with a polyvinylidene chloride resin.

For the heat-resistant resin substrate 21, for example, any film of various resins such as a polyolefin-based resin such as a polyethylene-based resin or a polypropylene-based resin, a cyclic polyolefin-based resin, a polystyrene-based resin, an acrylonitrile-styrene copolymer (AS resin), an acrylonitrile-butadiene-styrene copolymer (ABS resin), a poly(meth)acrylic-based resin, a polycarbonate-based resin, a polyester-based resin such as polyethylene terephthalate and polyethylene naphthalate, a polyamide-based resin such as various nylons, a polyurethane-based resin, an acetal-based resin, and a cellulose-based resin can be used. Among them, a film of a polyester-based resin, a polyolefin-based resin or a polyamide-based resin is preferable, and in particular, a film of biaxially oriented polypropylene, biaxially oriented polyethylene terephthalate or a biaxially oriented polyamide resin is preferable. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. The various resin films can be further uniaxially or biaxially oriented by utilizing, for example, a tentering method or a tubular method.

The thickness of the heat-resistant resin substrate 21 is preferably 3 to 500 μm, more preferably 5 to 300 μm, further preferably 10 to 100 μm, most preferably 15 to 50 μm.

The polyvinylidene chloride resin with which the heat-resistant resin substrate 21 is coated is preferably a homopolymer or copolymer of vinylidene chloride. As such a polymer, a vinylidene chloride copolymer where the content of vinylidene chloride is preferably in a range from 50 to 98% by mol, more preferably in a range from 75 to 96% by mol, is preferable because of being excellent in a balance between a film formation property and gas barrier property. As the monomer copolymerizable with vinylidene chloride, for example, vinyl chloride, acrylic acid esters such as methyl acrylate, ethyl acrylate, butyl acrylate, 2-ethylhexyl acrylate and 2-hydroxyethyl acrylate, methacrylic acid esters such as methyl methacrylate and glycidyl methacrylate, acrylonitrile, methacrylonitrile, and unsaturated carboxylic acids such as acrylic acid, methacrylic acid, itaconic acid and maleic acid can be selected and used singly or in combinations of two or more. Among them, vinyl chloride or acrylic acid ester is preferably used in terms of a film formation property. In addition, the polyvinylidene chloride resin can also be used in appropriate combinations of two or more. Furthermore, the polyvinylidene chloride resin, to which any additive such as a heat stabilizer, a light stabilizer, and a lubricant is appropriately added, can also be used. The polyvinylidene chloride resin is usually used as an emulsion or a solution.

Such a polyvinylidene chloride layer 22 can be formed by, for example, a method where the polyvinylidene chloride resin which is, if necessary, dissolved or dispersed in a solvent and thus formed into an application liquid is applied onto the surface of the heat-resistant resin substrate 21.

The thickness of the polyvinylidene chloride layer 22 is not particularly limited, may be appropriately set depending on the desired oxygen gas barrier property and the like, and is preferably 0.5 to 30 μm, more preferably 0.8 to 10 μm, most preferably 1 to 2 μm.

The oxygen permeability (20° C. and 90% RH) of the barrier layer by itself is preferably 1.5 to 20 cc/($m^2$·day·atm), more preferably 2.0 to 15 cc/($m^2$·day·atm), most preferably 2.0 to 10 cc/($m^2$·day·atm). In addition, the water vapor permeability (40° C. and 90% RH) of the barrier layer by itself is preferably 1.0 to 20 g/($m^2$·day), more preferably 2.5 to 15 g/($m^2$·day).

The oxygen permeability (20° C. and 90% RH) of the multilayer film for a disposable body warmer outer bag, including the sealant layer 10 and the barrier layer 20, of the present invention is preferably 1.5 to 5.0 cc/($m^2$·day·atm), more preferably 2.0 to 4.5 cc/($m^2$·day·atm), most preferably 2.5 to 4.0 cc/($m^2$·day·atm), and the water vapor permeability (40° C. and 90% RH) thereof is preferably 0.05 to 1.5 g/($m^2$~day), more preferably 0.05 to 1.0 g/($m^2$·day), most preferably 0.05 to 0.75 g/($m^2$·day). The multilayer film for a disposable body warmer outer bag, including the sealant layer 10 and the barrier layer 20, of the present invention can have such oxygen permeability and water vapor permeability in the above numerical ranges, to thereby exert the following effects: a gas barrier property that inhibits permeation of oxygen gas, water vapor and the like is excellent and swelling due to hydrogen gas generated during storage can be prevented.

Preferably, the adhesive layer 30 is provided between the sealant layer 10 and the barrier layer 20, and the sealant layer 10 and the barrier layer 20 are laminated with being bonded to each other. As the adhesive forming the adhesive layer, any adhesive usually used in the multilayer film for a disposable body warmer outer bag can be used without any limitation, and for example, an ether-based adhesive, a polyvinyl acetate-based adhesive, a polyacrylic acid ester-based adhesive made of a homopolymer of acrylic acid ethyl, butyl or 2-ethylhexyl ester, or a copolymer thereof with methyl methacrylate, acrylonitrile, styrene or the like, a cyanoacrylate-based adhesive, an ethylene copolymer-based adhesive made of a copolymer of ethylene with a monomer such as vinyl acetate, ethyl acrylate, acrylic acid or methacrylic acid, a cellulose-based adhesive, a polyester-based adhesive, a polyamide-based adhesive, a polyimide-based adhesive, an amino resin-based adhesive made of a urea resin, a melamine resin or the like, a phenol resin-based adhesive, an epoxy-based adhesive, a polyurethane-based adhesive, a reaction (meth)acrylic-based adhesive, a rubber-based adhesive made of a chloroprene rubber, a nitrile rubber, a styrene-butadiene rubber or the like, a silicone-based adhesive, an inorganic adhesive made of alkali metal silicate, low melting point glass or the like, or other adhesives can be used. The composition form of the adhesive may be any composition form such as an aqueous form, a solution form, an emulsion form and a dispersion form. In addition, the form of the adhesive may be any form such as a film-sheet form, a powder form and a solid form. Furthermore, the adhesion mechanism may be any mechanism such as chemical reaction, solvent volatilization, thermal fusion and thermal pressure mechanisms. Any mode usually used can be used as a usage mode of the adhesive without any limitation, and the adhesive layer can be formed by, for example, applying the adhesive onto at least one of the sealant layer 10 or the barrier layer 20 by a roll coating method, a gravure roll coating method, a kiss coating method, other coating methods, a printing method or the like, and then drying a solvent and the like. The content of the adhesive is preferably 0.1 to 10 g/$m^2$ (dry state), more preferably 0.5 to 8 g/$m^2$ (dry state), most preferably 1.5 to 4 g/$m^2$ (dry state).

In the multilayer film for a disposable body warmer outer bag of the present invention, the printing ink layer 40 may be provided as a constituent at any location. The printing ink layer 40 can be formed by adding one or more usual ink vehicles as a main component, arbitrarily adding, if necessary, one or more additives such as a plasticizer, a stabilizer, an antioxidant, a light stabilizer, an ultraviolet absorber, a curing agent, a crosslinking agent, a lubricant, an antistatic agent and a filler thereto, further adding a colorant such as a dye/pigment thereto, and sufficiently kneading the resultant with a solvent, a diluent or the like to prepare an ink composition; and then printing a desired character, graphic, sign, pattern and the like with the ink composition by use of, for example, gravure printing, offset printing, relief printing, screen printing, transfer printing, flexographic printing or other printing systems.

Any ink vehicle usually used for the disposable body warmer outer bag can be used as the ink vehicle without any limitation, and examples can include flaxseed oil, tung oil, soybean oil, hydrocarbon oil, rosin, rosin ester, a rosin-modified resin, shellac, an alkyd resin, a phenol-based resin, a maleic acid resin, a natural resin, a hydrocarbon resin, a polyvinyl chloride-based resin, a polyvinyl acetate-based resin, a polystyrene-based resin, a polyvinyl butyral resin, an acrylic or methacrylic-based resin, a polyamide-based resin, a polyester-based resin, a polyurethane-based resin, an epoxy-based resin, a urea resin, a melamine resin, an amino alkyd-based resin, nitrocellulose, ethyl cellulose, a chlorinated rubber and a cyclized rubber singly or in combinations of two or more.

The content of the printing ink layer 40 is preferably 0.1 to 10 g/m$^2$ (dry state), more preferably 0.5 to 8 g/m$^2$ (dry state), most preferably 1 to 5 g/m$^2$ (dry state).

The multilayer film for a disposable body warmer outer bag of the present invention may further include the additional resin layer 50. The additional resin layer 50 may be a layer formed from any resin as long as a gas permeation property and water vapor permeation property of the multilayer film for a disposable body warmer outer bag of the present invention are not impaired, and can be provided at any position. For example, the thermal fusible resin for use in the substrate of the sealant layer 10 or the heat-resistant resin for use in the substrate of the barrier layer 20 can be used. When the thermal fusible resin is used, it can be provided outward against the sealant layer 10 and used as a heat-sealing portion in formation of an outer bag. When the heat-resistant resin is used, it is preferably provided between the sealant layer 10 and the barrier layer 20, or opposite to the sealant layer 10 and outward against the barrier layer 20, namely, at a position corresponding to the outer surface of a disposable body warmer outer bag. When the heat-resistant resin is provided between the sealant layer 10 and the barrier layer 20, it enhances the strength of the multilayer film, and when it is provided at a position corresponding to the outer surface of a disposable body warmer outer bag, it functions as a protection film. The thickness of the additional resin layer 50 is not particularly limited, and is preferably 3 to 500 μm, more preferably 5 to 300 μm, further preferably 5 to 100 μm, most preferably 5 to 50 μm.

The multilayer film for a disposable body warmer outer bag of the present invention can preferably realize an oxygen permeability (20° C. and 90% RH) of 1.5 to 5.0 cc/(m$^2$·day·atm), more preferably 2.0 to 4.5 cc/(m$^2$·day·atm), most preferably 2.5 to 4.0 cc/(m$^2$·day·atm), and preferably realize a water vapor permeability (20° C. and 90% RH) of 0.05 to 1.5 g/(m$^2$·day), more preferably 0.05 to 1.0 g/(m$^2$·day), most preferably 0.05 to 0.75 g/(m$^2$·day). The multilayer film for a disposable body warmer outer bag of the present invention can have such oxygen permeability and water vapor permeability in the above numerical ranges, to thereby exert the following effects: a gas barrier property that inhibits permeation of oxygen gas, water vapor and the like is excellent and swelling due to hydrogen gas generated during storage can be prevented. In order to stably store a disposable body warmer for a long period, both the oxygen permeability and the water vapor permeability are required to be in the above ranges, and, if any one of the permeabilities is outside the range, no desired effects can be achieved.

Next, the method for producing each of the multilayer film for a disposable body warmer outer bag and the disposable body warmer outer bag of the present invention is described.

The multilayer film for a disposable body warmer outer bag of the present invention can be produced by pressure bonding of a vapor-deposited thermal fusible resin serving as the sealant layer 10, a heat-resistant resin coated with a polyvinylidene chloride resin, serving as the barrier layer 20, and an adhesive serving as the adhesive layer 30, as well as, if necessary, the printing ink layer 40 and the additional resin layer 50 being laminated, by use of a roll or the like.

Next, two of the multilayer films for disposable body warmer outer bag can be superposed so that the respective thermal fusible resin substrates 11 face each other, and the peripheries of the thermal fusible resin substrates 11 can be heat-sealed to form a bag, thereby producing a disposable body warmer outer bag. Any mode usually used can be used as the mode of heat-sealing without any limitation, and any heat-sealing form such as lateral sealing, two-side sealing, three-side sealing, four-side sealing, envelope-seam sealing, butt-seam sealing (pillow sealing), pleat sealing, flat bottom sealing, square bottom sealing, and gusset sealing forms may be adopted. Any heat-sealing method usually used can be used as the heat-sealing method without any limitation, and for example, bar sealing, rotating roll sealing, belt sealing, impulse sealing, high-frequency sealing, and ultrasonic sealing may be adopted.

The disposable body warmer of the present invention is made by packaging airtightly an inner bag accommodating an exothermic composition, in a disposable body warmer outer bag formed from the multilayer film for a disposable body warmer outer bag.

The exothermic composition may be an exothermic composition for use in a usual disposable body warmer, and is not particularly limited. For example, an exothermic composition may be adopted which contains metal powder such as iron powder, a reaction aid such as salt, activated carbon, a water-retaining agent, water and the like. Specifically, for example, an exothermic composition can be formed from 100 parts by weight of metal powder, for example, iron powder such as reduced iron powder or cast iron powder, or aluminum powder, 3 to 10 parts by weight of a reaction aid such as sodium chloride, 20 to 40 parts by weight of activated carbon and a water-retaining agent, 30 to 90 parts by weight of water, and the like. Herein, for example, an alkali metal hydroxide and a weakly basic alkali metal salt such as sodium hydroxide, potassium hydroxide, sodium hydrogen carbonate and sodium tertiary phosphate can be added as a hydrogen generation inhibitor to the exothermic composition, and the amount thereof to be used can be a trace amount relative to the metal powder.

In addition, the inner bag accommodating the exothermic composition may be air-permeable to such an extent that a metal can generate heat in the presence of oxygen, and for example, a bag article where one surface is prepared by an air-permeable packaging material and the other surface is prepared by an air-impermeable packaging material, or a bag article where both surfaces are each prepared by an air-permeable packaging material can be used. As the air-permeable packaging material, for example, a woven fabric or a non-woven fabric, a porous sheet where a plastic film, sheet or the like is perforated, or a composite sheet thereof can be used. In addition, as the air-impermeable packaging material, for example, a polyethylene-based resin, a polypropylene-based resin, an ethylene-propylene copolymer, an ethylene-vinyl acetate copolymer, an ionomer resin, an ethylene-ethyl acrylate copolymer, an ethylene-acrylic acid or methacrylic acid copolymer, a methylpentene polymer, a polybutene-based resin, a polyvinyl acetate-based resin, a poly(meth)acrylic-based resin, a polyacrylonitrile-based resin, a polystyrene-based resin, an acrylonitrile-styrene copolymer (AS-based resin), an acrylonitrile-butadiene-styrene copolymer (ABS-based resin), a polyester-based resin, a polyamide-based resin, a polycarbonate-based resin, a polyvinyl alcohol-based resin, a saponified product of an ethylene-vinyl acetate copolymer, a fluororesin, a diene-based resin, a polyacetal-based resin, a polyurethane-based resin, nitrocellulose, or other known resins or films can be used. Any commonly known method can be used as the method for producing the inner bag without any limitation, and for example, any of various heat-sealing methods described above with respect to production of the outer bag can be preferably used.

EXAMPLES

Hereinafter, the present invention is more specifically described with reference to Examples and Comparative Examples.

Example 1

A biaxially oriented polypropylene film having a polyvinylidene chloride layer (thickness: 21 μm, oxygen permeability: 8.1 cc/($m^2 \cdot day \cdot atm$), water vapor permeability: 5 g/($m^2 \cdot day$)) was adopted, and a character, a graphic, a sign, a picture and the like were printed on the polyvinylidene chloride layer by use of a usual gravure ink composition with a gravure printing system, thereby forming a printing ink layer. Next, an ether-based adhesive was applied onto the printing ink layer formed above, and dried to form an adhesive layer. An unoriented polypropylene film having an aluminum vapor-deposited layer (thickness: 25 μm, oxygen permeability: 10 cc/($m^2 \cdot day \cdot atm$), water vapor permeability: 0.5 g/($m^2 \cdot day$)) was placed on the adhesive layer so that the aluminum vapor-deposited layer and the adhesive layer were in contact with each other, and subjected to lamination and integration to produce a multilayer film for a disposable body warmer outer bag, including biaxially oriented polypropylene film/polyvinylidene chloride layer/printing ink layer/adhesive layer/aluminum vapor-deposited layer/unoriented polypropylene film.

Example 2

A multilayer film for a disposable body warmer outer bag, including biaxially oriented polyamide film/polyvinylidene chloride layer/printing ink layer/adhesive layer/aluminum vapor-deposited layer/unoriented polypropylene film, was produced in the same manner as in Example 1 except that a biaxially oriented polyamide film having a polyvinylidene chloride layer (thickness: 15 μm, oxygen permeability: 8.1 cc/($m^2 \cdot day \cdot atm$), water vapor permeability: 10 g/($m^2 \cdot day$)) was used instead of the biaxially oriented polypropylene film having a polyvinylidene chloride layer (thickness: 21 μm, oxygen permeability: 8.1 cc/($m^2 \cdot day \cdot atm$), water vapor permeability: 5 g/($m^2 \cdot day$)).

Example 3

A multilayer film for a disposable body warmer outer bag, including biaxially oriented polyethylene terephthalate film/polyvinylidene chloride layer/printing ink layer/adhesive layer/aluminum vapor-deposited layer/unoriented polypropylene film, was produced in the same manner as in Example 1 except that a biaxially oriented polyethylene terephthalate film having a polyvinylidene chloride layer (thickness: 12 μm, oxygen permeability: 8.1 cc/($m^2 \cdot day \cdot atm$), water vapor permeability: 10 g/($m^2 \cdot day$)) was used instead of the biaxially oriented polypropylene film having a polyvinylidene chloride layer (thickness: 21 μm, oxygen permeability: 8.1 cc/($m^2 \cdot day \cdot atm$), water vapor permeability: 5 g/($m^2 \cdot day$)).

Example 4

A biaxially oriented polyamide film having a polyvinylidene chloride layer (thickness: 15 μm, oxygen permeability: 8.1 cc/($m^2 \cdot day \cdot atm$), water vapor permeability: 10 g/($m^2 \cdot day$)) as a barrier layer was adopted, and a character, a graphic, a sign, a picture and the like were printed on the polyvinylidene chloride layer by use of a usual gravure ink composition with a gravure printing system, thereby forming a printing ink layer. Next, an ether-based adhesive was applied onto the printing ink layer formed above, and dried to form an adhesive layer. An unoriented polypropylene film having an aluminum vapor-deposited layer (thickness: 25 μm, oxygen permeability: 10 cc/($m^2 \cdot day \cdot atm$), water vapor permeability: 0.5 g/($m^2 \cdot day$)) was placed on the adhesive layer so that the aluminum vapor-deposited layer and the adhesive layer were in contact with each other, and subjected to lamination and integration. In addition, an ether-based adhesive was applied onto the biaxially oriented polyamide film, and dried to form a second adhesive layer. A biaxially oriented polypropylene film (thickness: 20 μm, oxygen permeability: 1500 cc/($m^2 \cdot day \cdot atm$), water vapor permeability: 8 g/($m^2 \cdot day$)) as an additional resin layer was placed on the second adhesive layer, and subjected to lamination and integration to produce a multilayer film for a disposable body warmer outer bag, including biaxially oriented polypropylene film/second adhesive layer/biaxially oriented polyamide film/polyvinylidene chloride layer/printing ink layer/adhesive layer/aluminum vapor-deposited layer/unoriented polypropylene film.

Examples 5 to 11

Each multilayer film for a disposable body warmer outer bag was produced in the same manner as in Example 4 except that each film shown in Table 1 below was used instead of the biaxially oriented polyamide film having a polyvinylidene chloride layer (thickness: 15 μm, 8.1 cc/($m^2 \cdot day \cdot atm$), water vapor permeability: 10 g/($m^2 \cdot day$)) as a barrier layer, and each film shown in Table 1 below was used instead of the biaxially oriented polypropylene film (thickness: 20 μm, oxygen permeability: 1500 cc/($m^2 \cdot day \cdot atm$), water vapor permeability: 8 g/($m^2 \cdot day$)) as an additional resin layer.

TABLE 1

|  | Barrier layer | Additional resin layer |
| --- | --- | --- |
| Example 5 | KPET#12 | OPP#20 |
| Example 6 | KOPP#20 | PET#12 |
| Example 7 | KONY#15 | PET#12 |
| Example 8 | KPET#12 | PET#12 |
| Example 9 | KOPP#20 | ONY#15 |

TABLE 1-continued

| | Barrier layer | Additional resin layer |
|---|---|---|
| Example 10 | KONY#15 | ONY#15 |
| Example 11 | KPET#12 | ONY#15 |

KPET#12: biaxially oriented polyethylene terephthalate film having polyvinylidene chloride layer (thickness: 12 μm, oxygen permeability: 8.1 cc/(m² · day · atm), water vapor permeability: 10 g/(m² · day))
KOPP#20: biaxially oriented polypropylene film having polyvinylidene chloride layer (thickness: 20 μm, oxygen permeability: 8.1 cc/(m² · day · atm), water vapor permeability: 5 g/(m² · day))
KONY#15: biaxially oriented polyamide film having polyvinylidene chloride layer (thickness: 15 μm, oxygen permeability: 8.1 cc/(m² · day · atm), water vapor permeability: 10 g/(m² · day))
OPP#20: biaxially oriented polypropylene film (thickness: 20 μm, oxygen permeability: 1500 cc/(m² · day · atm), water vapor permeability: 8 g/(m² · day))
PET#12: biaxially oriented polyethylene terephthalate film (thickness: 12 μm, oxygen permeability: 80 cc/(m² · day · atm), water vapor permeability: 50 g/(m² · day))
ONY#15: biaxially oriented polyamide film (thickness: 15 μm, oxygen permeability: 30 cc/(m² · day · atm), water vapor permeability: 250 g/(m² · day))

Comparative Example 1

A biaxially oriented polypropylene film having a polyvinylidene chloride layer (thickness: 21 μm, oxygen permeability: 8.1 cc/(m²·day·atm), water vapor, permeability: 5 g/(m²·day)) was adopted, and a printing ink layer and an adhesive layer were formed on the polyvinylidene chloride layer in the same manner as in Example 1. After a straight-chain low density polyethylene film (thickness: 30 μm, oxygen permeability: 5000 cc/(m²·day·atm), water vapor permeability: 16.6 g/(m²·day)) was placed on the adhesive layer, an adhesive layer was placed thereon in the same manner as above, and an ethylene-vinyl acetate copolymer film (thickness: 30 μm, oxygen permeability: 10000 cc/(m²·day·atm), water vapor permeability: 75 g/(m²·day)) was further placed thereon and subjected to lamination and integration to produce a multilayer film for a disposable body warmer outer bag, including biaxially oriented polypropylene film/polyvinylidene chloride layer/printing ink layer/adhesive layer/straight-chain low density polyethylene film/adhesive layer/ethylene-vinyl acetate copolymer film.

Comparative Example 2

A printing ink layer and an adhesive layer were formed on one surface of a biaxially oriented polypropylene film (thickness: 20 μm, oxygen permeability: 1500 cc/(m²·day·atm), water vapor permeability: 8 g/(m²·day)) in the same manner as in Example 1. A biaxially oriented polyethylene terephthalate film having an aluminum vapor-deposited layer (thickness: 12 μm, oxygen permeability: 1.5 cc/(m²·day·atm), water vapor permeability 1.7 g/(m²·day)) was placed on the adhesive layer so that the adhesive layer and the aluminum vapor-deposited layer were in contact with each other, and subjected to lamination and integration. Furthermore, an adhesive layer was formed on a surface of the biaxially oriented polyethylene terephthalate film having the aluminum vapor-deposited layer, the surface being opposite to the aluminum vapor-deposited layer, and thereafter a straight-chain low density polyethylene film (thickness: 30 μm, oxygen permeability: 5000 cc/(m²·day·atm), water vapor permeability: 16.6 g/(m²·day)) was placed thereon and subjected to lamination and integration to produce a multilayer film for a disposable body warmer outer bag, including biaxially oriented polypropylene film/printing ink layer/adhesive layer/aluminum vapor-deposited layer/biaxially oriented polyethylene terephthalate film/adhesive layer/straight-chain low density polyethylene film.

Comparative Example 3

A biaxially oriented polyethylene terephthalate film having a vapor-deposited layer of silicon oxide (thickness: 12 μm, oxygen permeability: 1.5 cc/(m²·day·atm), water vapor permeability 1.7 g/(m²·day)) was adopted, and a printing ink layer and an adhesive layer were formed on the vapor-deposited layer of silicon oxide in the same manner as in Example 1. An unoriented polypropylene film (thickness: 25 μm, oxygen permeability: 2400 cc/(m²·day·atm), water vapor permeability 14.4 g/(m²·day)) was placed on the adhesive layer, and subjected to lamination and integration to produce a multilayer film for a disposable body warmer outer bag, including biaxially oriented polyethylene terephthalate film/vapor-deposited layer of silicon oxide/printing ink layer/adhesive layer/unoriented polypropylene film.

Comparative Example 4

A multilayer film for a disposable body warmer outer bag, including biaxially oriented polyamide film/vapor-deposited layer of silicon oxide/printing ink layer/adhesive layer/unoriented polypropylene film, was produced in the same manner as in Comparative Example 3 except that a biaxially oriented polyamide film having a vapor-deposited layer of silicon oxide (thickness: 12 μm, oxygen permeability: 2.1 cc/(m²·day·atm), water vapor permeability 4.3 g/(m²·day)) was used instead of the biaxially oriented polyethylene terephthalate film having a vapor-deposited layer of silicon oxide (thickness: 12 μm, oxygen permeability: 1.5 cc/(m²·day·atm), water vapor permeability 1.7 g/(m²·day)).

Comparative Example 5

An ether-based adhesive was applied onto the biaxially oriented polyethylene terephthalate film forming the multilayer film for a disposable body warmer outer bag, obtained in Comparative Example 3, and dried to form a second adhesive layer. A biaxially oriented polypropylene film (thickness: 20 μm, oxygen permeability: 1500 cc/(m²·day·atm), water vapor permeability: 8 g/(m²·day)) was placed on the second adhesive layer and subjected to lamination and integration to produce a multilayer film for a disposable body warmer outer bag, including biaxially oriented polypropylene film/second adhesive layer/biaxially oriented polyethylene terephthalate film/vapor-deposited layer of silicon oxide/printing ink layer/adhesive layer/unoriented polypropylene film.

Comparative Example 6

A multilayer film for a disposable body warmer outer bag, including biaxially oriented polypropylene film/second adhesive layer/biaxially oriented polyethylene terephthalate film/vapor-deposited layer of silicon oxide/printing ink layer/adhesive layer/straight-chain low density polyethylene film was produced in the same manner as in Comparative Example 5 except that a straight-chain low density polyethylene film (thickness: 30 μm, oxygen permeability: 5000 cc/(m²·day·atm), water vapor permeability: 16.6 g/(m²·day)) was used instead of the unoriented polypropylene film (thickness: 25 μm, oxygen permeability: 2400 cc/(m²·day·atm), water vapor permeability: 14.4 g/(m²·day)).

(Evaluation)

The multilayer film for a disposable body warmer outer bag, produced in each of Example 1 and Comparative Examples 1 to 6, was used to evaluate the oxygen permeability, the water vapor permeability and the appearance as follows.

(1) Measurement of Oxygen Permeability

The following measurement machine was used under the following measurement conditions to measure the oxygen permeability (cc/(m$^2$·day·atm)) under the following temperature and humidity conditions.

Temperature: 20° C.; humidity: 90% RH

Measurement machine: OX-TRAN 2/20 manufactured by Mocon Inc.; measurement method: continuous measurement 20 times every 30 minutes (2) Measurement of Water Vapor Permeability The following measurement machine was used under the following measurement conditions to measure the water vapor permeability (g/(m$^2$·day)) under the following temperature and humidity conditions.

Temperature: 40° C.; humidity: 90% RH

Measurement machine: OX-TRAN 2/20 manufactured by Mocon Inc.; measurement method: continuous measurement 20 times every 30 minutes (3) Evaluation of Appearance after Acceleration Test Two of the multilayer films for disposable body warmer outer bag in each of Example 1 and Comparative Examples 1 to 6 were prepared, the thermal fusible substrates as sealant layers (Example 1 and Comparative Examples 3 to 5: unoriented polypropylene film; Comparative Example 1: ethylene-vinyl acetate copolymer film; Comparative Examples 2 and 6: straight-chain low density polyethylene film) were allowed to face and were superposed, and thereafter the outer peripheries thereof were subjected to three-side heat-sealing to form a sealing portion and also produce a three-side heat-sealed disposable body warmer outer bag having an opening portion on the upper portion thereof.

An exothermic composition including 22 g of iron powder, 6 g of activated carbon, 6 g of a water-retaining agent and 10 g of water was prepared, and the exothermic composition was then charged and packaged in an inner bag to produce a stick type disposable body warmer including an individual package. One surface of the inner bag is formed from a porous sheet of a perforated polyethylene film as an air-permeable packaging material and the other surface thereof is formed from a polyethylene film as an air-impermeable packaging material.

Next, the disposable body warmer including an individual package, produced above, was charged through the opening portion of the disposable body warmer outer bag produced above, and thereafter the opening portion was heat-sealed to form an upper sealing portion, thereby producing a disposable body warmer product.

Five of the disposable body warmer products thus obtained were placed on a stage, and the height (mm) of the five disposable body warmer products stacked (hereinafter, referred to as "height H1 (mm)".) was measured. Next, the five disposable body warmer products stacked were stored at a temperature of 50° C. for 3 months, and the height (mm) of the five disposable body warmer products stacked was measured every 1 week for a period of 3 months. The height after a lapse of 3 months was defined as "height H2 (mm)". If any outer bag of the disposable body warmer products was swollen and broken during such a storage period, however, the maximum height before such breakage was defined as "height H2 (mm)". The value "H2−H1 (mm)" was then calculated, and rated as the appearance after an acceleration test, according to the following criteria.

−2<*H*2−*H*1 (mm)<2: No change

−5<*H*2−*H*1 (mm)≤−2: Slightly depressurizing tendency

*H*2−*H*1 (mm)≤−5: Depressurizing tendency

*H*2−*H*1 (mm)<5: Slightly swelling tendency

5≤*H*2−*H*1 (mm): Swelling tendency (4) Evaluation of Exothermic Performance (Duration) after Acceleration Test A disposable body warmer product was produced in the same manner as in "(3) Evaluation of appearance after acceleration test" above.

The disposable body warmer outer bags of ten of the disposable body warmer products thus obtained were opened to take out respective disposable body warmers, and the exothermic performance of each of the disposable body warmers was tested based on JIS 54100. The duration average was defined as the "exothermic performance (duration)·initial" (hereinafter, referred to as "duration T1".).

On the other hand, ten of the disposable body warmer products obtained above were stored at a temperature of 50° C. for three months, thereafter respective disposable body warmer outer bags of the disposable body warmer products were opened to take out respective disposable body warmers, and the exothermic performance of each of the disposable body warmers was tested based on JIS 54100. The duration average was defined as "exothermic performance (duration)·after acceleration test" (hereinafter, referred to as "duration T2".).

The value T2/T1×100 (%) was then calculated, and rated as the exothermic performance (duration) in the evaluation after an acceleration test, according to the following criteria.

90<*T*2/*T*1×100 (%)≤100: A (Favorable)

80<*T*2/*T*1×100 (%)≤90: B (Usable)

*T*2/*T*1×100 (%)≤80: C (Not suitable as product)

Any heat-sealing portion was broken due to swelling, and heat generation was terminated before product opening:— (Not suitable as product)

TABLE 2

|  | Oxygen permeability (cc/(m$^2$ · day · atm)) | Water vapor permeability (g/(m$^2$ · day)) | H2-H1 (mm) | Evaluation of appearance | Exothermic performance (duration) |
| --- | --- | --- | --- | --- | --- |
| Example 1 | 3.7 | 0.5 | 0 | No change | A |
| Comparative Example 1 | 5.9 | 4.5 | −8 | Depressurizing tendency | C |
| Comparative Example 2 | 0.9 | 0.7 | 13 | Swelling tendency | — |
| Comparative Example 3 | 1.4 | 1.5 | 4 | Slightly swelling tendency | B |

TABLE 2-continued

|  | Oxygen permeability (cc/(m² · day · atm)) | Water vapor permeability (g/(m² · day)) | H2-H1 (mm) | Evaluation of appearance | Exothermic performance (duration) |
|---|---|---|---|---|---|
| Comparative Example 4 | 2.0 | 3.7 | −2 | Slightly depressurizing tendency | C |
| Comparative Example 5 | 1.4 | 1.2 | 4 | Slightly swelling tendency | B |
| Comparative Example 6 | 0.2 | 0.2 | 15 | Swelling tendency | — |

A disposable body warmer product, when rated as "No change", is not changed in appearance even after storage for a long period, and thus can be sold as a product in the market. On the other hand, a disposable body warmer product, when rated as "Slightly depressurizing tendency", "Depressurizing tendency", "Slightly swelling tendency" or "Swelling tendency", is changed in appearance after storage for a long period, and is not preferable.

As clear from the results in Table 2 above, in Example 1, no change in appearance of a package product was observed before and after an acceleration test and no degradation in exothermic function was caused even after storage for a long period. In addition, in Example 1, the disposable body warmer outer bag was low in water vapor permeability to allow water vapor to hardly penetrate, thereby allowing moisture to hardly penetrate from the exterior into the interior of the outer bag, and allowing moisture included as a component of the disposable body warmer to hardly escape to the outside, and therefore sufficiently served as a disposable body warmer even after storage for a long period. On the other hand, in all of Comparative Examples 1 to 6, a change in appearance of each package product was observed before and after an acceleration test, and each disposable body warmer product was not preferable in terms of appearance after storage for a long period. In addition, in Comparative Examples 1 and 4, each outer packaging material was slightly high in water vapor permeability to cause water vapor to easily penetrate, thereby causing moisture to easily penetrate from the exterior into the interior of the outer bag, and causing moisture included as an exothermic composition component of each disposable body warmer to easily escape to the outside, and therefore did not sufficiently generate heat as a disposable body warmer after storage for a long period. In addition, in Comparative Examples 2 and 6, swelling tendency was remarkably observed, and such swelling caused each heat-sealing portion to be broken, and each body warmer was brought into contact with outside air to terminate heat generation before each product was opened.

In addition, the exothermic composition was charged and packaged in an inner bag to produce a non-stick type disposable body warmer including an individual package. One surface of the inner bag is formed from a porous sheet of a perforated polyethylene film as an air-permeable packaging material and the other surface thereof is formed from a polyethylene film as an air-impermeable packaging material. Such a disposable body warmer was tested in the same manner as in Example 1, and favorable results were similarly obtained as in Example 1.

REFERENCE SIGNS LIST 10 sealant layer
11 thermal fusible resin substrate
12 vapor-deposited layer
20 barrier layer
21 heat-resistant resin substrate
22 polyvinylidene chloride layer
30 adhesive layer
40 printing ink layer
50 additional resin layer

The invention claimed is:

1. A multilayer film for a disposable body warmer outer bag, comprising:
   a thermal fusible resin substrate;
   a vapor-deposited layer on the thermal fusible resin substrate;
   a heat-resistant resin substrate; and
   a polyvinylidene chloride layer coated on the heat-resistant resin substrate,
   wherein the vapor-deposited layer is made by vapor-depositing a metal or metal oxide on the thermal fusible resin substrate, and
   the polyvinylidene chloride layer is made by coating the heat-resistant resin substrate with polyvinylidene chloride,
   wherein the vapor-deposited layer is in direct physical contact with the thermal fusible resin substrate, and the polyvinylidene chloride layer is in direct physical contact with the surface of the heat-resistant resin substrate,
   wherein an oxygen permeability of the multilayered film measured at 20° C. and 90% RH is 2.0 to 5.0 cc/(m²-day-atm), and a water vapor permeability of the multilayered film measured at 40° C. and 90% RH is 0.05 to 1.5 g/(m²-day),
   wherein the thermal fusible resin substrate comprises at least one resin selected from the group consisting of polypropylene and polyethylene, and the heat-resistant resin substrate comprises at least one resin selected from the group consisting of polyester-based resin, a polyolefin-based resin, and a polyamide-based resin, and
   wherein the thermal fusible resin substrate has a lower melting point than the heat-resistant resin substrate.

2. The multilayer film for a disposable body warmer outer bag according to claim 1, wherein
   the vapor-deposited layer is a sealant layer made by vapor-depositing a metal or metal oxide on at least one surface of the thermal fusible resin substrate, and
   the polyvinylidene chloride layer is a barrier layer made by coating at least one surface of the heat-resistant resin substrate with polyvinylidene chloride.

3. The multilayer film for a disposable body warmer outer bag according to claim 1, wherein
   the vapor-deposited layer is made by vapor-depositing a metal or metal oxide on the thermal fusible resin substrate selected from unoriented polypropylene, biaxially oriented polypropylene, unoriented polyethylene, low density polyethylene, medium density polyethylene, high density polyethylene and straight-chain (linear) low density polyethylene.

4. The multilayer film for a disposable body warmer outer bag according to claim 1, wherein
the vapor-deposited layer is made by vapor-depositing aluminum on the thermal fusible resin substrate selected from unoriented polypropylene, biaxially oriented polypropylene, unoriented polyethylene, low density polyethylene, medium density polyethylene, high density polyethylene and straight-chain (linear) low density polyethylene, and
the polyvinylidene chloride layer is made by coating the heat-resistant resin substrate selected from biaxially oriented polypropylene, biaxially oriented polyethylene terephthalate and biaxially oriented polyamide resins with a polyvinylidene chloride resin.

5. The multilayer film for a disposable body warmer outer bag according to claim 1, further comprising an adhesive layer between the vapor-deposited layer and the polyvinylidene chloride layer.

6. The multilayer film for a disposable body warmer outer bag according to claim 1, comprising an additional resin layer.

7. A disposable body warmer made by packaging airtightly an inner bag accommodating an exothermic composition, in an outer bag formed by thermal fusion of the multilayer film according to claim 1.

8. A method for keeping a shape of a disposable body warmer made by packaging airtightly an inner bag accommodating an exothermic composition, in an outer bag formed by thermal fusion of a multilayer film, the method comprising:
blocking a penetration of oxygen and water vapor from the exterior of the outer bag to the interior of the outer bag such that a metal in the exothermic composition is prevented from being oxidized;
preventing water vapor from being discharged from the interior of the outer bag to the exterior of the outer bag such that the outer bag is prevented from being depressed; and
permitting a penetration of hydrogen which is generated in the interior of the outer bag from the interior of the outer bag to the exterior of the outer bag such that the outer bag is prevented from being swollen, wherein
the multilayer film comprises:
a thermal fusible resin substrate;
a vapor-deposited layer on the thermal fusible resin substrate;
a heat-resistant resin substrate; and
a polyvinylidene chloride layer coated on the heat-resistant resin substrate,
wherein the vapor-deposited layer is made by vapor-depositing a metal or metal oxide on the thermal fusible resin substrate, and the polyvinylidene chloride layer is made by coating the heat-resistant resin substrate with polyvinylidene chloride,
wherein the vapor-deposited layer is in direct physical contact with the thermal fusible resin substrate, and the polyvinylidene chloride layer is in direct physical contact with the surface of the heat-resistant resin substrate,
wherein an oxygen permeability of the multilayered film measured at 20° C. and 90% RH is 2.0 to 5.0 cc/($m^2$-day-atm), and a water vapor permeability of the multilayered film measured at 40° C. and 90% RH is 0.05 to 1.5 g/($m^2$-day), and
wherein the thermal fusible resin substrate has a lower melting Point than the heat-resistant resin substrate.

* * * * *